(12) United States Patent
Lee et al.

(10) Patent No.: US 9,005,937 B2
(45) Date of Patent: Apr. 14, 2015

(54) DUAL COFACTOR SPECIFIC RIBITOL DEHYDROGENASE AND USE THEREOF

(75) Inventors: Jung Kul Lee, Seoul (KR); Hee Jung Moon, Seoul (KR); Manish Tiwari, Seoul (KR); Tae Su Kim, Seoul (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 0 days.

(21) Appl. No.: 13/880,374

(22) PCT Filed: Jan. 27, 2012

(86) PCT No.: PCT/KR2012/000623
§ 371 (c)(1),
(2), (4) Date: Apr. 18, 2013

(87) PCT Pub. No.: WO2013/065901
PCT Pub. Date: May 10, 2013

(65) Prior Publication Data
US 2014/0242642 A1    Aug. 28, 2014

(30) Foreign Application Priority Data

Oct. 31, 2011    (KR) .......................... 10-2011-111888

(51) Int. Cl.
| | | |
|---|---|---|
| *C12P 19/02* | (2006.01) | |
| *C12N 9/00* | (2006.01) | |
| *C12N 9/04* | (2006.01) | |
| *C12N 1/20* | (2006.01) | |
| *C12N 15/00* | (2006.01) | |
| *C07H 21/04* | (2006.01) | |

(52) U.S. Cl.
CPC .............. *C12P 19/02* (2013.01); *C12N 9/0006* (2013.01); *C12Y 101/01056* (2013.01)

(58) Field of Classification Search
None
See application file for complete search history.

(56) References Cited

PUBLICATIONS

Accession Q5NQS1. Feb. 1, 2005.*
Moon, H. J. et al., "Cloning and characterization of a ribitol dehydrogenase from *Zymomonas mobilis*," Applied Microbiology and Biotechnology. vol. 87(1), pp. 205-214 (Feb. 2, 2010).
Moon, H. J. et al., "Molecular determinants of the cofactor specificity of ribitol dehydrogenase, a short-chain dehydrogenase/reductase," Applied and Environmental Microbiology. vol. 78(9), pp. 3079-3086 (Feb. 17, 2012).
Reid, M. F. and Fewson, C. A., "Molecular characterization of microbial alcohol dehydrogenases' Critical Reviews in Microbiology," vol. 20(1), pp. 13-56 (1994).
De Muynck, C. et al., "Dehydrogenation of ribitol with *Gluconobacter oxydans*: production and stability of L-ribulose," Journal of Biotechnology. vol. 125(3), pp. 408-415 (May 2, 2006).
GenBank Accession No. AAG02162: ribitol dehydrogenase [*Zymomonas mobilis* subsp. mobilis ZM4] (Aug. 28, 2000).
Osao Adachi et al., "Membrane-bound Sugar Alcohol Dehydrogenase in Acetic Acid Bacteria catalyzes L-Ribulose Formation and NAD-Dependent Ribitol Dehydrogenase is Independent of the Oxidative Fermentation" Biosci Biotechnol Biochem, vol. 65, No. 1, pp. 115-125 (Jan. 2001).
Moon, Hee Jung, Ph. D Thesis, "Metabolic Engineering of *Escherichia coli* forα-Lipoic Acid Production—Protein Engineering of a Ribitol Dehydrogenase from *Zymomonas mobilis*", Jun. 2011.

* cited by examiner

*Primary Examiner* — Christian Fronda
(74) *Attorney, Agent, or Firm* — Lexyoume IP Meister, PLLC (57) ABSTRACT

There are provided a novel ribitol dehydrogenase, a residue determining double coenzyme specificity, and a method for preparing L-ribulose using the same, and more particularly, to a ribitol dehydrogenase producing rare sugars, nucleic acid molecules encoding the same, a vector including the nucleic acid molecules, a transformant including the vector, a mutant of the ribitol dehydrogenase, and a method for preparing L-ribulose using the ribitol dehydrogenase. The ribitol dehydrogenase having double coenzyme specificity, which is derived from *Zymomonas mobilis*, can effectively be used for preparing high-priced rare sugars and an investigation of coenzyme specificity determinants for the ribitol dehydrogenase is applied for all of dedydrogenases as a based technique.

2 Claims, 5 Drawing Sheets

SEQUENCE LISTING

```
<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: primer

<400> SEQUENCE: 1
attaggatcc atgataccgc gccccgatca                                          30

<210> SEQ ID NO 2
<211> LENGTH: 31
<212> TYPE: DNA
<213> ORGANISM: Artificial Sequence
<220> FEATURE:
<223> OTHER INFORMATION: primer

<400> SEQUENCE: 2
tatactcgag aaaaatctgg gcgcatccgg t                                        31

<210> SEQ ID NO 3
<211> LENGTH: 795
```

<212> TYPE: DNA
<213> ORGANISM: Zymomonas mobilis

<400> SEQUENCE: 3

```
atgataccgc gccccgatca tggtgaaaaa agctatcgcg gttccggcaa attacaaggt      60
cggaaggctt tgattacggg tggtgattcc ggcatcggtc gggcaacagc gattgcctat     120
gcccgtgaag gcgcggatat tgttatcaat tatttgccgc aagaagagcc ggatgcccgc     180
gaagttgtcg ctttgttaca gggagaaggt cataaggttt ttgccttgcc cggtgatttg     240
agaaatgaaa atttctgtgt ccagctcgtt caggaagcct ccaagcgttt gggcggacta     300
gatattttgg cgaatattgc cggacatcag cattataatg aatctatcct gacgctttcg     360
acggctgatt ttgatgatac cttgaaaacc aatgtttatg cgatgttttg gttgtgcaag     420
gaagccttga aaatcatgcc tgccggttcg gcaattgtga ataccagctc aacacagggc     480
tatcgacctt cggctatttt attggattat gccaccagca aagcggctat tgccaatttt     540
acccgcgctt ggctatccaa actggcacct agaggtattc gagtgaatgc cgtggcaccg     600
ggcccgtttt ggacaccgct tcaggtatcg ggcggtcagc ctgcctctgc ttatagtcaa     660
tttggtgcca atacgccggt taaacgtccc ggtcagccgg ttgaaatcgc accggtttat     720
gtcttttttgg cttgtgccga aaatagctat gtgacgggtg aagtctatgg cgttaccgga     780
tgcgcccaga ttttt                                                     795
```

<210> SEQ ID NO 4
<211> LENGTH: 265
<212> TYPE: PRT
<213> ORGANISM: Zymomonas mobilis

<400> SEQUENCE: 4

```
Met Ile Pro Arg Pro Asp His Gly Glu Lys Ser Tyr Arg Gly Ser Gly
 1               5                  10                  15

Lys Leu Gln Gly Arg Lys Ala Leu Ile Thr Gly Gly Asp Ser Gly Ile
            20                  25                  30

Gly Arg Ala Thr Ala Ile Ala Tyr Ala Arg Glu Gly Ala Asp Ile Val
        35                  40                  45

Ile Asn Tyr Leu Pro Gln Glu Glu Pro Asp Ala Arg Glu Val Val Ala
    50                  55                  60

Leu Leu Gln Gly Glu Gly His Lys Val Phe Ala Leu Pro Gly Asp Leu
65                  70                  75                  80

Arg Asn Glu Asn Phe Cys Val Gln Leu Val Gln Glu Ala Ser Lys Arg
                85                  90                  95

Leu Gly Gly Leu Asp Ile Leu Ala Asn Ile Ala Gly His Gln His Tyr
            100                 105                 110

Asn Glu Ser Ile Leu Thr Leu Ser Thr Ala Asp Phe Asp Asp Thr Leu
        115                 120                 125

Lys Thr Asn Val Tyr Ala Met Phe Trp Leu Cys Lys Glu Ala Leu Lys
    130                 135                 140

Ile Met Pro Ala Gly Ser Ala Ile Val Asn Thr Ser Ser Thr Gln Gly
145                 150                 155                 160

Tyr Arg Pro Ser Ala Ile Leu Leu Asp Tyr Ala Thr Ser Lys Ala Ala
                165                 170                 175

Ile Ala Asn Phe Thr Arg Ala Leu Ala Ile Gln Leu Ala Pro Arg Gly
            180                 185                 190

Ile Arg Val Asn Ala Val Ala Pro Gly Pro Phe Trp Thr Pro Leu Gln
        195                 200                 205
```

```
Val Ser Gly Gly Gln Pro Ala Ser Ala Tyr Ser Gln Phe Gly Ala Asn
        210                 215                 220

Thr Pro Val Lys Arg Pro Gly Gln Pro Val Glu Ile Ala Pro Val Tyr
225                 230                 235                 240

Val Phe Leu Ala Cys Ala Glu Asn Ser Tyr Val Thr Gly Glu Val Tyr
                245                 250                 255

Gly Val Thr Gly Cys Ala Gln Ile Phe
                260                 265

<210> SEQ ID NO 5
<211> LENGTH: 265
<212> TYPE: PRT
<213> ORGANISM: Artificial Sequence
<220> FEATURE:
<223> OTHER INFORMATION: mutant

<400> SEQUENCE: 5

Met Ile Pro Arg Pro Asp His Gly Glu Lys Ser Tyr Arg Gly Ser Gly
1               5                   10                  15

Lys Leu Gln Gly Arg Lys Ala Leu Ile Thr Gly Gly Asp Ser Gly Ile
            20                  25                  30

Gly Arg Ala Thr Ala Ile Ala Tyr Ala Arg Glu Gly Ala Asp Ile Val
        35                  40                  45

Ile Asn Tyr Leu Pro Gln Glu Pro Asp Ala Arg Glu Val Val Ala
    50                  55                  60

Leu Leu Gln Gly Glu Gly His Lys Val Phe Ala Leu Pro Gly Asp Leu
65                  70                  75                  80

Arg Asn Glu Asn Phe Cys Val Gln Leu Val Gln Glu Ala Ser Lys Arg
                85                  90                  95

Leu Gly Gly Leu Asp Ile Leu Ala Asn Ile Ala Gly His Gln His Tyr
            100                 105                 110

Asn Glu Ser Ile Leu Thr Leu Ser Thr Ala Asp Phe Asp Asp Thr Leu
        115                 120                 125

Lys Thr Asn Val Tyr Ala Met Phe Trp Leu Cys Lys Glu Ala Leu Lys
    130                 135                 140

Ile Met Pro Ala Gly Ser Ala Ile Val Asn Thr Asp Ser Thr Gln Gly
145                 150                 155                 160

Tyr Arg Pro Ser Ala Ile Leu Leu Asp Tyr Ala Thr Ser Lys Ala Ala
                165                 170                 175

Ile Ala Asn Phe Thr Arg Ala Leu Ala Ile Gln Leu Ala Pro Arg Gly
            180                 185                 190

Ile Arg Val Asn Ala Val Ala Pro Gly Pro Phe Trp Thr Pro Leu Gln
        195                 200                 205

Val Ser Gly Gly Gln Pro Ala Ser Ala Tyr Ser Gln Phe Gly Ala Asn
    210                 215                 220

Thr Pro Val Lys Arg Pro Gly Gln Pro Val Glu Ile Ala Pro Val Tyr
225                 230                 235                 240

Val Phe Leu Ala Cys Ala Glu Asp Ser Tyr Val Thr Gly Glu Val Tyr
                245                 250                 255

Gly Val Thr Gly Cys Ala Gln Ile Phe
                260                 265

<210> SEQ ID NO 6
<211> LENGTH: 265
<212> TYPE: PRT
<213> ORGANISM: Artificial Sequence
```

```
<220> FEATURE:
<223> OTHER INFORMATION: mutant

<400> SEQUENCE: 6

Met Ile Pro Arg Pro Asp His Gly Glu Lys Ser Tyr Arg Gly Ser Gly
1               5                   10                  15

Lys Leu Gln Gly Arg Lys Ala Leu Ile Thr Gly Gly Asp Ser Gly Ile
            20                  25                  30

Gly Arg Ala Thr Ala Ile Ala Tyr Ala Arg Glu Gly Ala Asp Ile Val
        35                  40                  45

Ile Asn Asp Leu Pro Gln Glu Glu Pro Asp Ala Arg Glu Val Val Ala
    50                  55                  60

Leu Leu Glu Gly Glu Gly His Lys Val Phe Ala Leu Pro Gly Asp Leu
65                  70                  75                  80

Arg Asn Glu Asn Phe Cys Val Gln Leu Val Gln Glu Ala Ser Lys Arg
                85                  90                  95

Leu Gly Gly Leu Asp Ile Leu Ala Asn Ile Ala Gly His Gln His Tyr
            100                 105                 110

Asn Glu Ser Ile Leu Thr Leu Ser Thr Ala Asp Phe Asp Asp Thr Leu
        115                 120                 125

Lys Thr Asn Val Tyr Ala Met Phe Trp Leu Cys Lys Glu Ala Leu Lys
    130                 135                 140

Ile Met Pro Ala Gly Ser Ala Ile Val Asn Thr Ala Ser Thr Gln Gly
145                 150                 155                 160

Tyr Arg Pro Ser Ala Ile Leu Leu Asp Tyr Ala Thr Ser Lys Ala Ala
            165                 170                 175

Ile Ala Asn Phe Thr Arg Ala Leu Ala Ile Gln Leu Ala Pro Arg Gly
            180                 185                 190

Ile Arg Val Asn Ala Val Ala Pro Gly Pro Phe Trp Thr Pro Leu Gln
            195                 200                 205

Val Ser Gly Gly Gln Pro Ala Ser Ala Tyr Ser Gln Phe Gly Ala Asn
    210                 215                 220

Thr Pro Val Leu Arg Pro Gly Gln Pro Val Glu Ile Ala Pro Val Tyr
225                 230                 235                 240

Val Phe Leu Ala Cys Ala Glu Asn Ser Tyr Val Thr Gly Glu Val Tyr
            245                 250                 255

Gly Val Thr Gly Cys Ala Gln Ile Phe
            260                 265
```

DUAL COFACTOR SPECIFIC RIBITOL DEHYDROGENASE AND USE THEREOF

TECHNICAL FIELD

The present invention relates to a novel ribitol dehydrogenase, a residue determining double coenzyme specificity, and a method for preparing L-ribulose using the same, and more particularly, to a ribitol dehydrogenase producing rare sugars, nucleic acid molecules encoding the same, a vector including the nucleic acid molecules, a transformant including the vector, a mutant of the ribitol dehydrogenase, and a method for preparing L-ribulose using the ribitol dehydrogenase.

BACKGROUND ART

A redox enzyme is frequently used for synthesizing a fine chemical product, medicine and medical supplies, food additives, herbicides, or the like, which has an industrial high value. The redox enzyme requires a coenzyme such as nicotinamide adenine dinucleotide (including a reduced type and phosphate, that is, NAD(H) and NADP(H)) to have activity. A coenzyme is a low-molecular substance and an essential material for an enzyme reaction. Especially, a pyridine-based coenzyme is widely used. A reaction using the redox enzyme requires a continuous supply of coenzyme to produce a product, but there is a problem in that the cost of the coenzyme is very high. In order to solve the aforementioned problem, many researchers are studying on a regeneration of a coenzyme, and also on methods for effectively using the coenzyme by finding residues in relation to coenzyme specificity.

Recently, uses of L-carbohydrates and nucleoside derivatives thereof are dramatically on the increase in a medical field. Especially, some modified nucleosides exhibit a considerable potential as a useful antiviral agent. L-ribose is an important core pentose constituting a frame for synthesizing L-ribonucleoside, L-oligoribonucleoside, and many other treating agents. Since L-nucleoside has high stability from an attack of nucleases in the body as compared with D-nucleoside, L-nucleoside is a candidate substance having high potential in being used as a material for treating. Since L-ribose is known to have high usefulness as a production raw material that is the basis of medicine and medical supplies, such as an antiviral agent and anticancer drug, L-ribose has been noticed in recent years and thereby establishment of high efficiency biological production method of L-ribose is required.

Despite the aforementioned importance and usefulness, unlike D-ribose, L-ribose is present in a small quantity over the natural world, and also even though a method for producing L-ribose is known, a relatively high cost ($1,000/kg) is required. Accordingly, there is a need for a method that is capable of commercially producing L-ribose at low cost.

Some chemical methods for converting L-arabinose, D-glucose, L-xylose, D-galactose, and D-ribose into L-ribose derivatives are known (Matteson, D. S, and Peterson, M. L. (1987) J. Org. Chem., 52(23), 5116-5121; Yamaguchi, M. and Mukaiyama, T. (1981) Chem. Lett., 7, 1005-1008). However, the methods have disadvantages, such as low yield, needs for a high-priced starting material, many reaction steps, difficulty of mass synthesis, and the like. In addition, the methods take long-period time due to a series of chemical reactions; require relatively high-priced chemicals; generate unnecessary by-products; and are labor intensive methods. Accordingly, an attempt for biochemically producing L-ribose from L-ribulose using a microorganism and an enzyme thereof has been made (Shimonishi, T., Izumori, K., J. (1996) J. Ferment. Bioeng. 81, 493-497). It is expected that the above disadvantage can be overcome by using an enzymatic production method for producing L-ribose using the biocatalizer described above.

Korean Patent Publication No. 1020090081435, a relevant prior patent, relates to "a thermal resistance L-ribose isomerase and a method for producing the same," in which the thermal resistance L-ribose isomerase acts as a production of L-ribulose by isomerizing L-ribose having a molecular weight of 32,000 (SDS-PAGE), the optimum temperature of 45° C., the optimum pH of 9.0 (glycine-NaOH buffer solution), and a stable physicochemical property of temperature stability to 45° C. upon being thermal-treated for 10 minutes at pH 9.0, or inversely as a production of L-ribose by isomerizing L-ribulose. In addition, the above Korean Patent Publication No. 1020090081435 discloses a conversion method of aldose and ketose, in which a thermal resistance L-ribose isomerase that is an enzyme derived from Raoultella ornithinolytica MB426 (NITE BP-277) is reacted with the aldose selected from L-ribose, D-lyxose, D-talose, D-mannose, L-allose, and L-gulose, thereby isomerizing the aldose and then producing the ketose selected from the corresponding L-ribulose, D-xylulose, D-tagatose, D-fructose, L-fucose, and L-sorbose, respectively or the L-ribose isomerase is reacted with the ketose selected from L-ribulose, D-xylulose, D-tagatose, D-fructose, L-fucose, and L-sorbose, thereby isomerizing the ketose and then producing the aldose selected from the corresponding L-ribose, D-lyxose, D-talose, D-mannose, L-allose, and L-gulose, respectively.

Korean Patent Publication No. 1020100053294, a relevant prior patent, relates to "a novel L-arabinose isomerase and a method for producing L-ribulose using the same," and more particularly, to L-arabinose isomerase expressed from a gene of a novel L-arabinose isomerase derived from *Bacillus licheniformis* strain having arabinose isomerase activity, a method for producing L-arabinose isomerase from the strain transformed by a recombinant expression vector including the above gene, and a method for producing L-ribulose using the above enzyme.

DISCLOSURE

Technical Problem

The present invention is invented to solve the aforementioned problems and with the aforementioned necessity, and the first object of the present invention is to provide a gene of a ribitol dehydrogenase derived from *Zymomonas mobilis*.

The second object of the present invention is to provide a ribitol dehydrogenase expressed from the above gene.

The third object of the present invention is to provide a recombinant expression vector including the gene of ribitol dehydrogenase.

The fourth object of the present invention is to provide all of the transformed strains including a transformed recombinant *E. coli*.

The fifth object of the present invention is to provide a recombinant ribitol dehydrogenase using a transformed recombinant *E. coli*.

The sixty object of the present invention is to suggest a residue determining double coenzyme specificity using the enzyme.

The seventh object of the present invention is to provide a method for producing L-ribulose from ribitol using the enzyme.

Other objects and advantages of the present invention will be described more clearly with reference to the following detailed description, claims and drawings.

Technical Solution

In order to achieve the above objects, the present invention provides a ribitol dehydrogenase having an amino acid sequence as set forth in SEQ ID NO: 4 or a functional fragment thereof.

According to an exemplary embodiment of the present invention, the ribitol dehydrogenase is preferably derived from *Zymomonas mobilis*, but the present invention is not limited thereto.

In addition, according to a preferable exemplary embodiment of the present invention, the ribitol dehydrogenase is specific to ribitol.

According to an exemplary embodiment of the present invention, the ribitol dehydrogenase is preferably specific to a double coenzyme for NAD(H) and NADP(H), but the present invention is not limited thereto.

According to an exemplary embodiment of the present invention, preferably, a molecular weight of the enzyme of the present invention is 28 kDa and an optimum enzyme reaction pH of the enzyme is 9.0 to 10.5, but the present invention is not limited thereto.

In addition, activity of the enzyme of the present invention increases when $Mn^{2+}$ or $Co^{2+}$ is present.

In addition, the present invention provides a gene of a ribitol dehydrogenase, in which the gene encodes the enzyme described above.

The gene of the present invention has preferably a base sequence as set forth in SEQ ID NO: 3, and also the sequence having at least 85% or more of sequence identity with the sequence as set forth in SEQ ID NO: 3, preferably at least 90% or more, and more preferably 95% or more is preferable in view of a degeneracy of a gene code, and the like, but the present invention is not limited thereto.

The present invention provides a method for preparing a ribitol dehydrogenase by culturing the strain transformed by a recombinant expression vector including the gene of ribitol dehydrogenase according to the present invention.

In addition, the present invention provides a ribitol dehydrogenase mutant selected from the group consisting of a) a mutant, in which serine, an amino acid at position 156 of the ribitol dehydrogenase having an amino acid sequence as set forth in SEQ ID NO: 4 is substituted with aspartic acid; and b) a mutant, in which tyrosine, an amino acid at position 51 of the ribitol dehydrogenase having an amino acid sequence as set forth in SEQ ID NO: 4 is substituted with aspartic acid and serine, an amino acid at position 156 is substituted with alanine.

The mutants have preferably amino acid sequences as set forth in SEQ ID NOS: 5 and 6, respectively, but the present invention is not limited thereto.

The present invention provides a based technique on an investigation of determinants of coenzyme specificity by suggesting some residues having double coenzyme specificity using the ribitol dehydrogenase according to the present invention.

In addition, the present invention provides a method for preparing L-ribulose from ribitol using the wide-type ribitol dehydrogenase of the present invention or a mutant thereof.

Best Mode

Hereinafter, the present invention will be described.

The present invention relates to a novel ribitol dehydrogenase, a residue determining double coenzyme specificity, and a ribitol dehydrogenase capable of producing L-ribulose from ribitol. In addition, the present invention provides a based technique on an investigation of determinants of coenzyme specificity by suggesting some residues having double coenzyme specificity using the enzyme described above.

The ribitol dehydrogenase of the present invention has an amino acid sequence as set forth in SEQ ID NO: 4. In addition, the ribitol dehydrogenase according to the present invention includes a mutated ribitol dehydrogenase introduced at least one mutation, such as deletion, substitution, and addition of at least one amino acid in the range, in which activity of the ribitol dehydrogenase as set forth in the protein having the amino acid sequence as set forth in SEQ ID NO: 4 is not impaired.

Further, the present invention relates to one including a gene of ribitol dehydrogenase encoding the ribitol dehydrogenase having an amino acid sequence as set forth in SEQ ID NO: 4 and represented by SEQ ID NO: 3 as the gene sequence thereof. Furthermore, the gene of ribitol dehydrogenase according to the present invention includes the mutated gene of ribitol dehydrogenase encoding the above mutated ribitol dehydrogenase obtained by mutating a base sequence as set forth in SEQ ID NO: 3.

In addition, the present invention includes a recombinant vector including the gene of ribitol dehydrogenase, and transformants transformed by the recombinant vector. In addition, the present invention includes a method for preparing a ribitol dehydrogenase, in which the method includes isolating the ribitol dehydrogenase from a culture obtained by culturing the transformants.

Hereinafter, the present invention will be described in more detail.

A gene of the ribitol dehydrogenase according to the present invention is isolated from a strain, *Zymomonas mobilis*. First, a chromosome DNA is obtained from a strain having a gene of ribitol dehydrogenase. As a method for isolating the chromosome DNA, a known method may be used.

As a vector, a phage vector or plasmid vector capable of being autonomically proliferated in a host microorganism may be used. Examples of the phage vector or cosmid vector include pWE15, M13, EMBL3, EMBL4, FIXII, DASHII, ZAPII, gt10, gt11, Charon4A, Charon21A, and the like and examples of the plasmid vector include pBR-based, pUC-based, pBluescriptII-based, pGEM-based, pTZ-based, pET-based, and the like. In addition to the above examples, various shuttle vectors, such as vectors capable of being autonomically proliferated in multiple host microorganisms, such as *E. coli* or *Pseudomonas* genus may also be used. For the above vectors, a desired fragment may be obtained by cleaving a gene with a suitable restriction enzyme as described above.

An introduction of a recombinant vector into a host microorganism is performed by using a known method. For example, in the case of using *E. coli* as a host microorganism, there is a calcium chloride method (Journal of Molecular Biology, vol. 53, page 159, 1970), a rubidium chloride method (Methods in Enzymology, vol. 68, page 253, 1979), an electroporation method (Current Protocols in Molecular Biology, vol. 1, page 184, 1994), or the like as an available method. Further, in the case of using a cosmid vector or phage vector, a transduction may be performed by using an in vitro packaging method (Current Protocols in Molecular Biology, vol. 1, page 571, 1994), or the like. Furthermore, it is possible to use a method using a transfer replication.

Next, a probe for obtaining a DNA fragment including a gene of ribitol dehydrogenase of *Zymomonas mobilis* strain is prepared. With a base sequence of the ribitol dehydrogenase gene, oligonucleotides from a base sequence as set forth in SEQ ID NO: 3 is produced. It is possible to synthesize these oliogonucleotides by using a custom synthesis service manufactured by Amersham-pharmacia Biotech, for example.

Next, a polymerase chain reaction (hereinafter, referred to as "PCR") is performed by using the produced oligonucleotides as a primer and a chromosome DNA of *Zymomonas mobilis* strain as a template to partially amplify the gene of ribitol dehydrogenase. The PCR amplified fragment thus obtained is a fragment having almost 100% identity with the gene of ribitol dehydrogenase of *Zymomonas mobilis* strain. Therefore, the fragment is expected to have high S/N ratio as a probe when colony hybridization is performed, and also is possible to easily control a stringency of hybridization. The PCR amplified fragment is marked with a suitable reagent and colony hybridization is performed to the chromosome DNA library to select a gene of ribitol dehydrogenase (Current Protocols in Molecular Biology, vol. 1, page 603, 1994).

A DNA fragment including a gene of ribitol dehydrogenase may be obtained by collecting plasmid through an alkali method (Current Protocols in Molecular Biology, vol. 1, page 161, 1994) from *E. coli* selected from any one of the above methods. It is to use a Sanger's sequencing method (Molecular Cloning, vol. 2, page 133, 1989), and the like, for example and also a dye primer method or dye terminator method using DNA Sequencer, such as DNA Sequencer 377A (Perkin Elmer), for example to determine a base sequence of the DNA fragment.

In addition, after the whole base sequence is determined by the above method, it is possible to obtain the gene of the present invention by hybridizing, as a probe, the DNA fragment prepared by any one of a chemical synthesis method, a PCR method using a chromosome DNA as a template, a digestion of the DNA fragment having the above base sequence through a restriction enzyme, or the like.

A base sequence of the gene of ribitol dehydrogenase according to the present invention is represented by SEQ ID NO: 3 and an amino acid sequence encoding the above gene is represented by SEQ ID NO: 4. However, as described above, some, for example 1 or several amino acids may be modified by deletion, substitution, addition, and the like as long as the polypeptide having the above amino acid sequence has activity of ribitol dehydrogenase. The gene according to the present invention is added to a gene having a base sequence encoding an amino acid as set forth in SEQ ID NO: 4 and includes a degenerate isomer encoding the same polypeptide that is different for degenerate codon. At this time, the mutation by deletion, substitution, addition, and the like may be introduced by using a site-directed mutagenesis introduction method (Current Protocols in Molecular Biology, vol. 1, page 811, 1994), and the like.

The transformed microorganism of the present invention is obtained by introducing the recombinant vector of the present invention into the host that is suitable for the expression vector that is used for manufacturing the recombinant vector. For example, in the case of using a bacterium such as *E. coli* as a host, it is preferable that the recombinant vector of the present invention be capable of being autonomically replicated in the host and also have a configuration required for an expression of transcription termination sequence and DNA including a gene of ribitol dehydrogenase and a promoter. pGEX-KG is used as the expression vector used for the present invention, but any one of the expression vectors may be used as long as the vector satisfies the above-described requirements.

Any one of the promoters may be used as long as the promoter can be expressed in a host, and may include, for example, promoters derived from *E. coli* or a phage, such as a trp promoter, a trc promoter, a lac promoter, a PL promoter, a PR promoter, a T7 promoter, a T3 promoter, and the like. The calcium chloride method, electroporation method, and the like as described above may be used as a method for introducing a recombinant DNA into a bacterium.

In addition, it is possible to use a recombinant vector having a fragment for suppressing an expression, in which the vector has various functions for suppressing, amplifying, or inducing an expression, a marker for selecting transformants, a resistance gene to antibiotics, a gene encoding a signal for the purpose of secretion out of a strain, and the like.

A preparation of the ribitol dehydrogenase according to the present invention is performed, for example, by culturing transformants obtained through transforming a host using a recombinant vector having a gene encoding the ribitol dehydrogenase; producing and accumulating the ribitol dehydrogenase that is a gene product in a culture (cultured cell bodies or cultured supernatant); and then obtaining the ribitol dehydrogenase from the culture.

A method for culturing the transformants of the present invention may include a typical method used for culturing a host.

In addition, when the microorganism transformed by using an inducible expression vector is cultured by a promoter, an inducer that is suitable for a type of promoter is added to a medium. Examples of the inducer may include isopropyl-D-thiogalactopyranoside (IPTG), tetracycline, indoleacrylic acid (IAA), and the like.

Obtainment and purification of the ribitol dehydrogenase may be performed by using singly or in combination of two or more kinds of a cell destruction system, extraction, affinity chromatography, cation or anion exchange chromatography, a gel filtration, and the like after centrifuging and collecting a cell body or supernatant from the resulting culture.

Whether or not the resulting purified substance is a desired enzyme may be confirmed by a general method, for example, SDS-polyacrylamide gel electrophoresis, western blotting, and the like.

In addition, culture of transformant using a microorganism as a host, production of a ribitol dehydrogenase by the transformant, accumulation of the ribitol dehydrogenase in cell bodies, and collection of the ribitol dehydroganse from the cell bodies are not limited to the above methods.

The present inventors cloned a gene of ribitol dehydrogenase from *Zymomonas mobilis* to suggest some residues having double coenzyme specificity. It could be found that a based technique on an investigation of determinant of coenzyme specificity may be provided by suggesting some residues, in which the recombinant strain inserted with the cloned gene has double coenzyme specificity. In addition, the present inventors found that the recombinant strain inserted with the gene may produce L-ribulose from ribitol and also may not produce by-products. Thus, the inventors finally completed the present invention.

According to the present invention, the gene encoding a ribitol dehydrogenase is cloned from a gene of *Zymomonas mobilis* to prepare the ribitol dehydrogenase that is industrially useful and a base sequence of the gene and an amino acid sequence assumed from the base sequence are analyzed.

The ribitol dehydrogenase of the present invention catalyzes a dehydrogenation reaction using ribitol as a substrate to produce L-ribulose, and more preferably, means a ribitol dehydrogenase having ability capable of converting ribitol to L-ribulose through the dehydrogenation reaction.

The ribitol dehydrogenase of the present invention has the following properties: (i) an optimum pH of 9.0 to 10.5; (ii) a molecular weight of about 28 kDa; (iii) increase of activity in the presence of $Mn^{2+}$ or $Co^{2+}$; and (iv) double coenzyme specificity.

Preferably, the ribitol dehydrogenase of the present invention has an optimum pH of 9.0 to 10.0, and more preferably about 9.5.

The ribitol dehydrogenase of the present invention has the maximum enzyme activity in the presence of 10 mM of $Mn^{2+}$ or $Co^{2+}$. According to the present invention, the obtained ribitol dehydrogenase derived from *Zymomonas mobilis* has, with regard to coenzyme NAD, a $K_m$ value of about 0.18 mM, a $k_{cat}$ value of about 4.84 $sec^{-1}$, and a $k_{cat}/k_m$ value of 27.3 $sec^{-1}$ $mM^{-1}$. In addition, the ribitol dehydrogenase has, with regard to coenzyme NADP, a $K_m$ value of about 0.26 mM, a $k_{cat}$ value of about 2.79 $sec^{-1}$, and a $k_{cat}/k_m$ value of 10.8 $sec^{-1}$ $mM^{-1}$. The ribitol dehydrogenase has double coenzyme specificity unlike other dehydrogenases.

Universally, in order for a redox enzyme to have activity, only one of NAD(H) and NADP(H) is needed as a coenzyme, but the ribitol dehydrogenase of the present invention may use both of NAD(H) and NADP(H) as a coenzyme. Therefore, the enzyme of the present invention exhibiting double coenzyme specificity is very special. Then, the present invention provides a based technique on an investigation of determinant of coenzyme specificity by suggesting some residues having double coenzyme specificity. In addition, by using various mutants exhibiting coenzyme specificity, ribitol is specifically converted into L-ribulose, thereby usefully applying the coenzyme to production of L-ribulose from sugar mixture.

Effect of Invention

L-ribulose produced by the ribitol dehydrogenase of the present invention is an intermediate for synthesizing L-ribose, and the L-ribose is an important core pentose constituting a frame for synthesizing L-ribonucleoside, L-oligoribonucleoside, and many other treatment agents. The nucleoside induced as mentioned above has the considerable potential as a useful antiviral agent. In addition, a supply of the based technique on an investigation of determinant of coenzyme specificity by suggesting some residues having double coenzyme specificity may be applied to all of dehydrogenases.

Hereinafter, the present invention will be described in more detail with reference to the following Examples, but the present invention is not limited to the following Examples.

Example 1

Gene Cloning of Ribitol Dehydrogenase

Zymomonas mobilis (ATCC 31821, Biological Resource Center, Korea Research Institute of Bioscience and Biotechnology, Korea) was cultured at 30° C. and centrifuged (8000×g for 10 minutes) to obtain cell bodies. A genome DNA was isolated from the obtained body cells. Primers, ZmRDH F-5' ATT AGG ATC CAT GAT ACC GCG CCC CGA TCA-3' (SEQ ID NO: 1) and ZmRDH R-5' TAT ACT CGA GAA AAA TCT GGG CGC ATC CGG T-3' (SEQ ID NO: 2) were manufactured by using a base sequence of a gene encoding a dehydrogenase of Zymomonas mobilis and then a PCR was performed. A product of the PCR, that is, the gene including the ribitol dehydrogenase amplified from Zymomonas mobilis was inserted into a pGEM T-easy vector to analyze a base sequence (SEQ ID NO: 3).

Example 2

Preparation of Recombinant Expression Vector and Recombinant Strain

In order to express a ribitol dehydrogenase in E. coli in bulk using the gene encoding the ribitol dehydrogenase according to Example 1, the enzyme gene was inserted to an Xho site and BamH site of an expression vector, pGEX-KG (Promega, U.S.A.), and then E. coli BL21 (DE3) (NEB, United Kingdom) was transformed.

Example 3

Expression and Pure Isolation of Recombinant Ribitol Dehydrogenase

Figure 1:
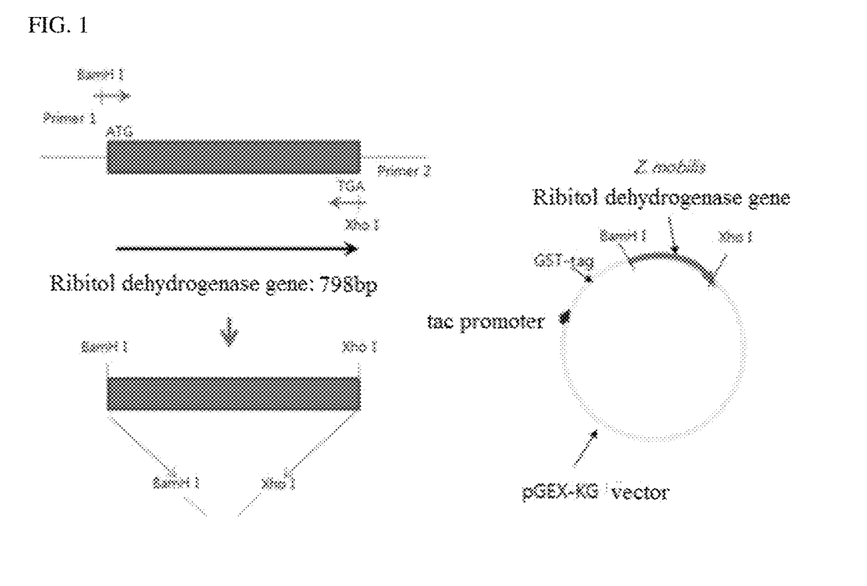
FIG. 1 is a diagram illustrating a method for preparing an expression vector including a gene of ribitol dehydrogenase derived from a strain, Zymomonas mobilis.
Figure 2:
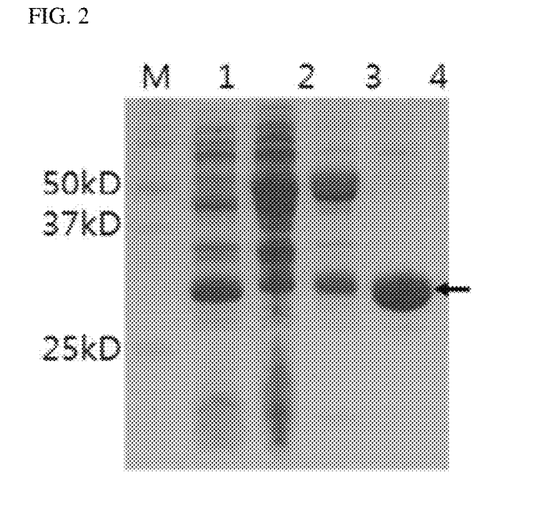
FIG. 2 shows a SDS-PAGE gel image of the ribitol dehydrogenase derived from a strain, Zymomonas mobilis.

The recombinant strain prepared in Example 2 was inoculated into a LB medium and cultured at 37° C. for 24 hours, and then the expressed proteins were confirmed on a SDS-PAGE gel (FIG. 2).

In order to purify the recombinant ribitol dehydrogenase expressed by using the method of Example 3, the culture solution of recombinant strain was centrifuged (8000×g for 10 minutes) to collect only cell bodies and the resulting cell bodies was sonicated to destruct a cell wall of E. coli. Then, it was centrifuged at 20,000×g for 20 minutes to remove the precipitate (cell bodies) and then obtain the supernatant. Subsequently, the supernatant was heated at 70° C. for 15 minutes, and centrifuged at 20,000×g for 20 minutes to remove the precipitate and then obtain the supernatant. Finally, the supernatant was subjected to a column chromatography using a Glutathione Sepharose 4B column (GE Healthcare, United Kingdom) to purely isolate the recombinant ribitol dehydrogenase. In addition, GST-tag was removed from the purely isolated ribitol dehydrogenase using a Thrombin cleavage kit (Novagen, Germany) (FIG. 2).

Example 4

Property Experiment of Ribitol Dehydrogenase

Physicochemical properties of the ribitol dehydrogenase isolated in Example 4 were investigated using ribitol as a substrate.

Example 4-1

Optimum pH

Figure 3:
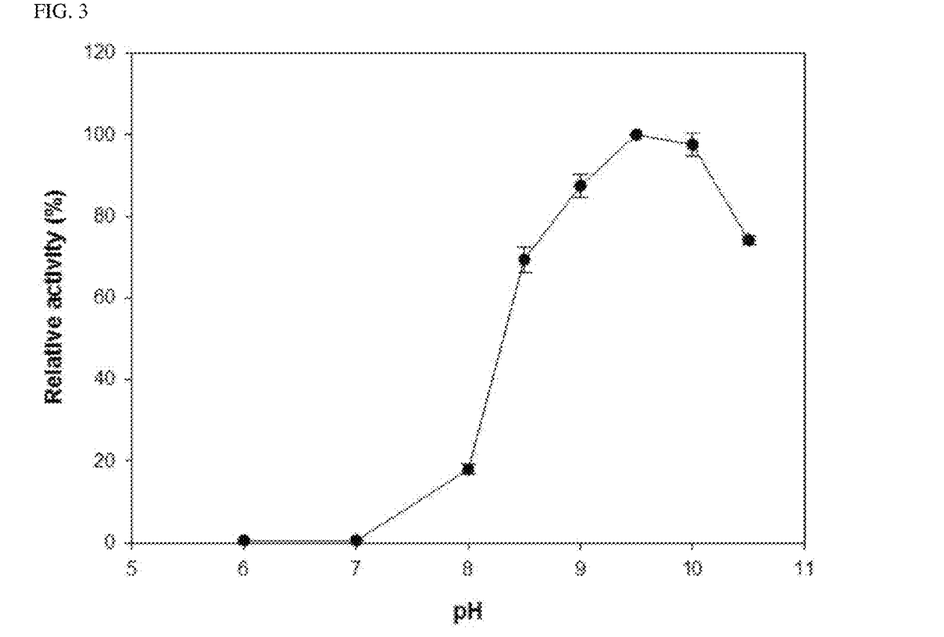
FIG. 3 is a graph illustrating reaction activity according to pH of the ribitol dehydrogenase derived from a strain, Zymomonas mobilis.

The optimum pH on dehydrogenation activity of the ribitol dehydrogenase was measured using 20 mM of Tris-HCl buffer. The enzyme activity was determined by monitoring the change per minute in absorbance at 340 nm while the sample was reacted in the presence of NAD(H) and ribitol. As illustrated in FIG. 3, the optimum pH of the ribitol dehydrogenase was 9.5 and 80% or more of the highest level of activity was maintained at pH 9.0 to 10.5 (FIG. 3).

Example 4-2

Effect of Metal Ion

EDTA of final concentration of 10 mM was treated to the purely purified enzyme and maintained for 24 hours. Then, after dialyzing the enzyme solution thus obtained with 20 mM of Tris-HCl buffer, the resulting enzyme solution was used for the present experiment. The remained activity of enzyme along with $MgCl_2$, $MnCl_2$, $CoCl_2$, $ZnCl_2$, $CaCl_2$, $FeSO_4$, $CuSO_4$, KCl, $HgCl_2$, or $BaCl_2$ which has final concentration of 10 mM was measured. Effects of various metals having a concentration of 10 mM on the activity of ribitol dehydrogenase are listed in Table 1. When $Mn^{2+}$ or $Co^{2+}$ was added, the activity of enzyme was observed, but when other metal ions were present, the activity of enzyme was not observed.

TABLE 1

| Metal ion | Relative activity (%) 10 mM |
|---|---|
| None | — |
| EDTA | — |
| MnCl$_2$ | 100 |
| CoCl$_2$ | 62.5 |
| CaCl$_2$ | 1.1 |
| ZnCl$_2$ | 0.3 |
| MgCl$_2$ | 0.4 |
| CuSO$_4$ | 0.1 |
| FeCl$_3$ | 0.2 |
| HgCl$_2$ | — |
| BaCl$_2$ | — |

Example 4-4

Dynamical Parameter of Ribitol Dehydrogenase to Coenzyme

The enzyme reaction was performed as Example 4-1 using a coenzyme, NAD(H) or NADP(H) (0.1 to 2 mM) of various concentrations. Then, dynamical parameters were measured through a nonlinear regression analysis (Table 2). For the ribitol dehydrogenase derived from *Zymomonas mobilis*, it was determined that with regard to a coenzyme, NAD(H), the $K_m$ value was 0.18 mM, the $K_{cat}$ value was about 4.83 sec$^{-1}$, and the $K_{cat}/K_m$ value was 27.3 sec$^{-1}$ mM$^{-1}$. It was determined that with regard to a coenzyme, NADP(H), the $K_m$ value was 0.26 mM, the $K_{cat}$ value was about 2.79 sec$^{-1}$, and the $K_{cat}/K_m$ value was 10.8 sec$^{-1}$ mM$^{-1}$. The ribitol dehydrogenase corresponds an enzyme having double coenzyme specificity among the redox enzymes that are reported up to now.

TABLE 2

| Coenzyme | | | | | |
|---|---|---|---|---|---|
| NAD(H) | | | NADP(H) | | |
| $k_{cat}$ (s$^{-1}$) | $K_{m, NAD}$ (mM) | $k_{cat}/K_{m, NAD}$ (S$^{-1}$ mM$^{-1}$) | $k_{cat}$ (s$^{-1}$) | $K_{m, NADP}$ (mM) | $k_{cat}/K_{m, NADP}$ (S$^{-1}$ mM$^{-1}$) |
| 4.83 | 0.18 | 27.3 | 2.79 | 0.26 | 10.8 |

Example 5

Preparation of Variant of Ribitol Dehydrogenase Having Double Coenzyme Specificity Example 5-1

Confirmation of Residue Having Double Coenzyme Specificity

Figure 4:
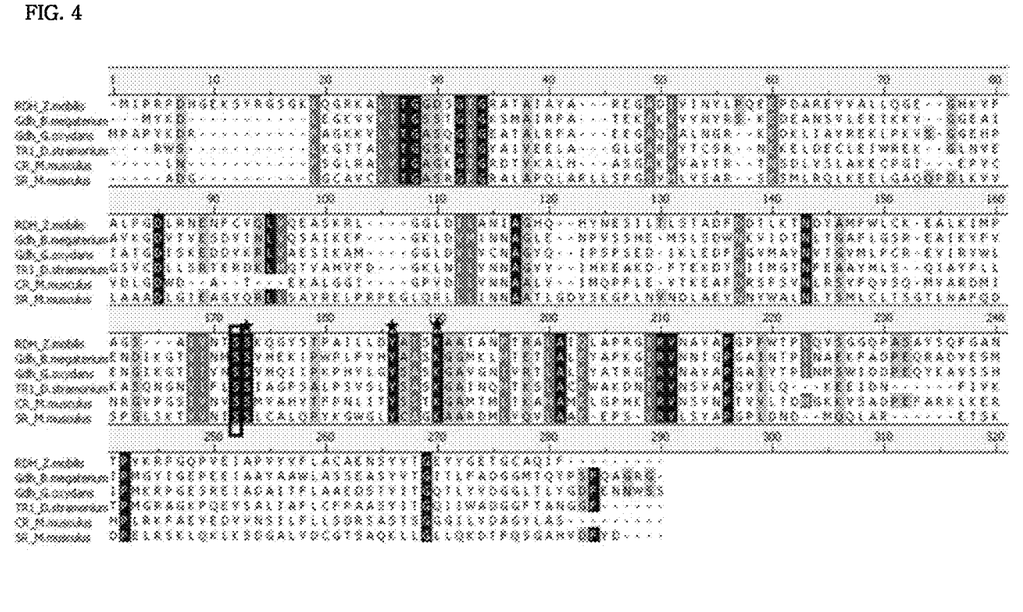
FIG. 4 is a diagram illustrating analysis of multiple sequence alignment with a redox enzyme using NADP(H) as a coenzyme.

An analysis was performed through a multiple sequence alignment in order to search residues having double coenzyme specificity using the ribitol dehydrogenase that was purely isolated in Example 3. As illustrated in FIG. 4, it was observed that when the multiple sequence alignment analysis with the redox enzyme using NADP(H) as a coenzyme was performed, a Ser residue at position 156 exactly corresponded.

Example 5-2

Alanine Substitution of Ser 156 and Measurement of Enzyme Activity

As described in Example 5-1, when the multiple sequence alignment analysis with the redox enzyme using NADP(H) as a coenzyme was performed, the corresponding Ser residue at position 156 was substituted with alanine. A S156A variant was prepared by using a site-directed mutagenesis kit (Stratagene, U.S.A.). As described in Table 3, it was observed that the S156A variant had significantly decreased enzyme activity on a coenzyme, NADP. Thus, it was supposed to secure the Ser 156 residue variant through a site-directed mutagenesis method.

TABLE 3

| | NAD(H) | | NADP(H) | |
|---|---|---|---|---|
| Coenzyme | Wide-type | S156A | Wide-type | S156A |
| Relative activity (%) | 100 | 100 | 42.9 | 15.4 |

Example 5-3

Preparation of Ser156 Variant

As described in Example 5-1, when the multiple sequence alignment analysis with the redox enzyme using NADP(H) as a coenzyme was performed, the corresponding Ser residue at position 156 was substituted with other amino acid residues using the same method as Example 5-2. There were no differences between the expression amount of various amino acid variants of Ser 156 and the expression amount of wide-type. The dynamical parameter of each of variants was confirmed using the above variants.

Example 5-4

Dynamic Parameter of Ser156 Variant

The enzyme reaction was performed as Example 4-1 using a coenzyme, NAD or NADP (0.01 to 3 mM) of various concentrations. Then, dynamical parameters were measured through a nonlinear regression analysis. The dynamical parameter for the ribitol dehydrogenase derived from *Zymomonas mobilis* to a coenzyme are listed in Table 4. It was observed that when for each of the variants, Kcat/Km ratio was compared with that of wide-type, the coenzyme specificity was changed by substituting a Ser residue at position 156. Especially, S156D variant exhibited significant difference of Kcat/Km ratio as compared with S156H variant. From this result, it could be found that the Ser residue at position 156 of the ribitol dehydrogenase derived from *Zymomonas mobilis* was involved in the double coenzyme specificity.

TABLE 4

| | NAD+ | | | NADP+ | | | |
|---|---|---|---|---|---|---|---|
| | $K_{m,NAD}$ (mM) | $k_{cat}$ (s$^{-1}$) | $k_{cat}/K_{m,NAD}$ (s$^{-1}$ mM$^{-1}$) | $K_{m,NADP}$ (mM) | $k_{cat}$ (s$^{-1}$) | $k_{cat}/K_{m,NADP}$ (s$^{-1}$ mM$^{-1}$) | $[k_{cat}/K_m]_{NAD}/[k_{cat}/K_m]_{NADP}$ |
| Wild-type | 0.18 ± 0.02 | 4.83 ± 0.51 | 27.3 | 0.26 ± 0.02 | 2.79 ± 0.15 | 10.8 | 2.36 |
| S156A | 0.19 ± 0.02 | 1.93 ± 0.16 | 10.2 | 0.39 ± 0.13 | 1.19 ± 0.07 | 3.05 | 3.34 |
| S156G | 0.14 ± 0.01 | 1.04 ± 0.02 | 7.43 | 0.34 ± 0.07 | 0.72 ± 0.08 | 2.12 | 3.51 |
| S156T | 0.21 ± 0.06 | 2.85 ± 0.10 | 13.6 | 0.22 ± 0.03 | 1.64 ± 0.22 | 7.45 | 1.83 |
| S156C | 0.10 ± 0.02 | 2.00 ± 0.09 | 20.0 | 0.17 ± 0.02 | 2.05 ± 0.10 | 12.1 | 1.66 |
| S156Y | 0.15 ± 0.01 | 1.60 ± 0.13 | 10.7 | 0.23 ± 0.13 | 1.42 ± 0.16 | 6.17 | 1.73 |
| S156W | 0.16 ± 0.02 | 2.62 ± 0.11 | 16.4 | 0.21 ± 0.03 | 2.05 ± 0.11 | 9.76 | 1.68 |
| S156D | 0.02 ± 0.002 | 1.79 ± 0.01 | 89.5 | 0.30 ± 0.03 | 2.46 ± 0.21 | 8.20 | 10.9 |
| S156E | 0.05 ± 0.003 | 2.06 ± 0.07 | 41.2 | 0.35 ± 0.04 | 2.39 ± 0.15 | 6.83 | 6.03 |
| S156R | 0.27 ± 0.02 | 2.93 ± 0.22 | 10.9 | 0.05 ± 0.001 | 2.75 ± 0.11 | 55.0 | 0.20 |
| S156H | 0.40 ± 0.05 | 3.22 ± 0.14 | 8.05 | 0.03 ± 0.002 | 2.29 ± 0.01 | 76.3 | 0.11 |
| S156K | 0.24 ± 0.03 | 3.10 ± 0.15 | 12.9 | 0.09 ± 0.008 | 3.10 ± 0.23 | 34.4 | 0.37 |

Example 6

Figure 5:
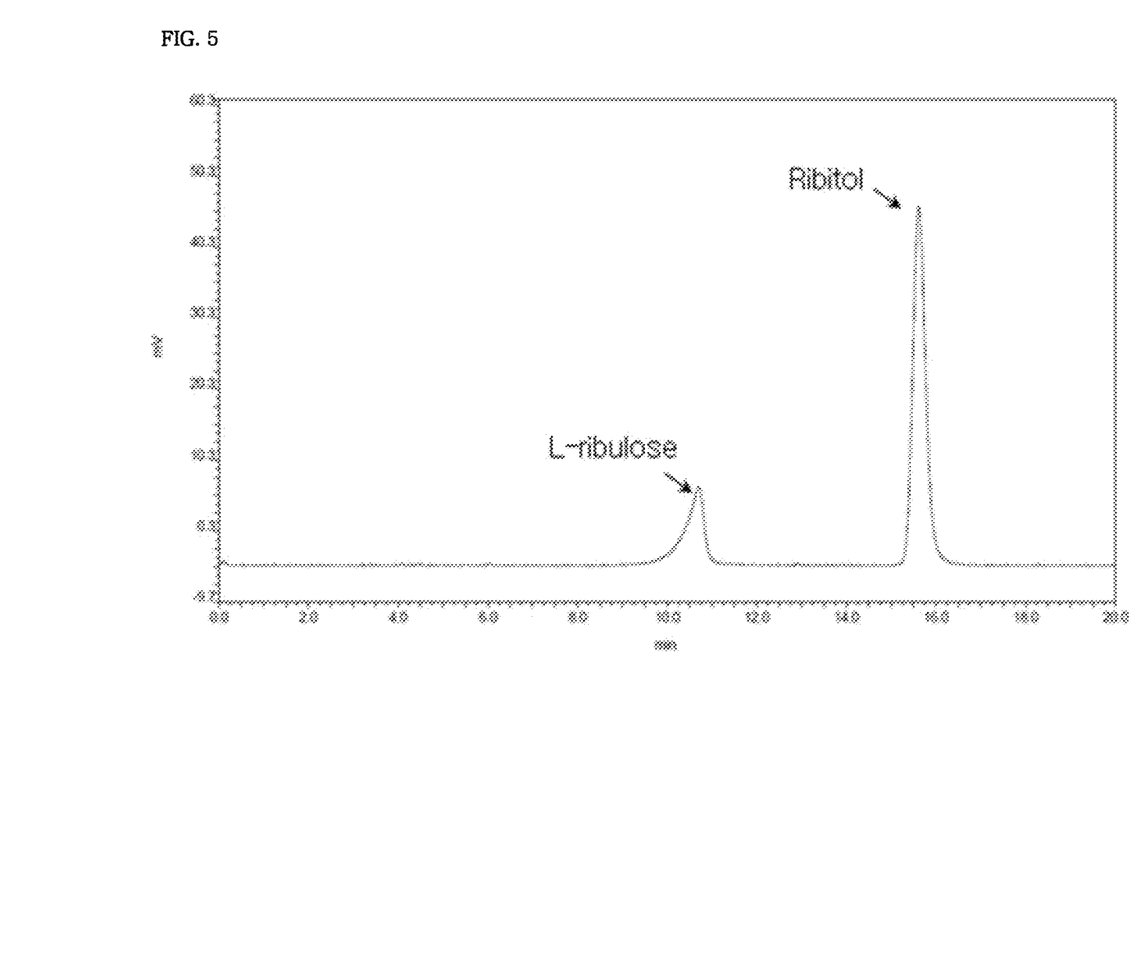
FIG. 5 shows results of analyzing, by using a high-performance liquid chromatography (HPLC), whether or not L-ribulose is only produced from ribitol without any by-products when L-ribulose is produced using a ribitol dehydrogenase.
Figure 6:
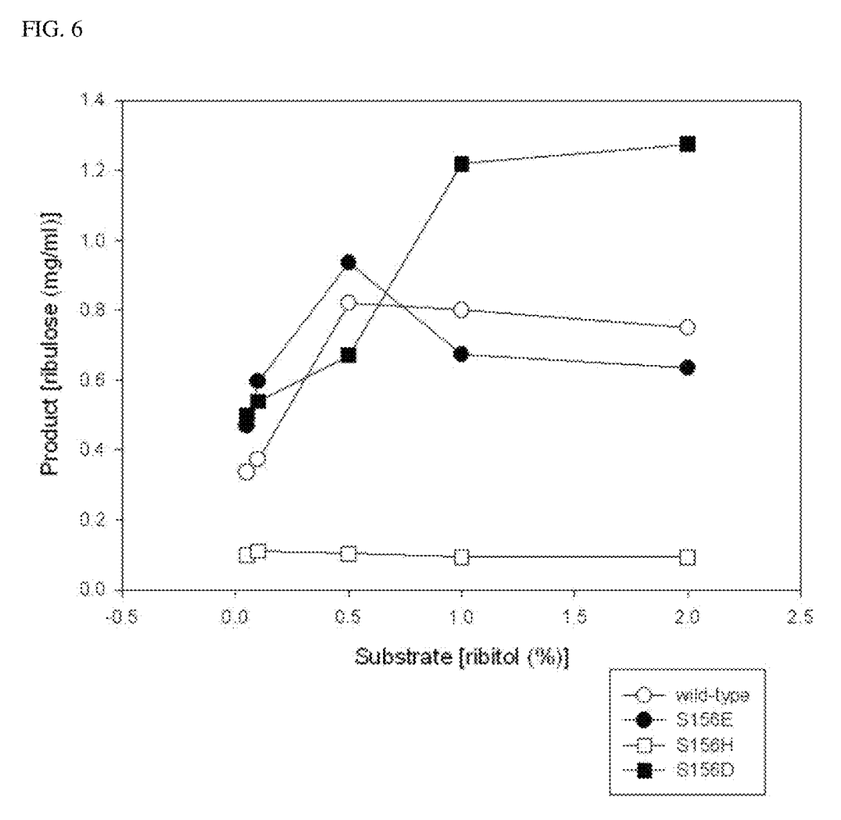
FIG. 6 is a diagram illustrating an amount of L-ribulose produced using a cell body obtained from a strain, Zymomonas mobilis.

Method of Preparing L-Ribulose Using Ribitol Dehydrogenase Variant Having Double Coenzyme Specificity The following experiments were performed in order to produce L-ribulose using a ribitol dehydrogenase variant having double coenzyme specificity. The variants prepared by using the method of Example 5-3 were expressed using the method of Example 2; the cell bodies were only collected by centrifuging (8000×g for 10 minutes) the recombinant strain culture solution; and then the cell bodies were washed with distilled water twice. The final Cell OD was measured and the same amount of cells was used for a production experiment. The ribitol and each of recombinant enzyme variants were subjected to an enzyme reaction in 20 mM of Tris-HCl buffer (pH 9.5) at a temperature of 25° C. for 6 hours. The enzyme reaction was stopped through a centrifuge, and then as illustrated in FIG. 3, when L-ribulose was produced using the ribitol dehydrogenase, whether L-ribulose was only produced from the ribitol was analyzed using an ELSD detector and a high-performance liquid chromatography (HPLC) having a cosmosil column. The production of L-ribulose according to the ribitol dehydrogenase variants are shown in FIG. 5.

As a result, while the wild-type produced L-ribulose in a concentration of 0.80 g/l, the S156E and S156D variants produced L-ribulose in concentrations of 0.93 g/l and 1.21 g/l, respectively. In the case of using S156E and S156D variants having coenzyme specificity to NAD, the conversion rate of L-ribulose in the whole cell level was higher than that of wild-type. On the contrary, it could be found that with regard to the S156H variant having coenzyme specificity to NADP, the conversion rate of L-ribulose significantly decreased as compared with that of wild-type. This means that in the case of the variant having coenzyme specificity to NAD, the conversion of L-ribulose was effectively progressed in the whole cell level. Thus, according to the method for a conversion of L-ribulose using the ribitol dehydrogenase having double coenzyme specificity of the present invention, L-ribulose can be produced with excellent yield and high concentration as compared with the method for producing L-ribulose using only the conventional wild-type.

The invention claimed is:

1. A ribitol dehydrogenase mutant, in which serine, an amino acid at position 156 of the ribitol dehydrogenase having an amino acid sequence as set forth in SEQ ID NO: 4 is substituted with aspartic acid.

2. A method for preparing L-ribulose from ribitol comprising reacting the mutant according to claim 1 with ribitol in 20 mM of Tris-HCl buffer (pH 9.5) at 25° C. for 6 hours.

* * * * *